(12) United States Patent
Hart et al.

(10) Patent No.: US 7,342,657 B2
(45) Date of Patent: Mar. 11, 2008

(54) DUAL ILLUMINATION ANGLE GONIOMETRIC SPECTROPHOTOMETER

(75) Inventors: Robert H. Hart, Cary, NC (US); David R. Battle, Durham, NC (US); Michael R. Groh, Raleigh, NC (US)

(73) Assignee: GretagMacbeth, LLC, New Windsor, NY (US)

( * ) Notice: Subject to any disclaimer, the term of this patent is extended or adjusted under 35 U.S.C. 154(b) by 0 days.

(21) Appl. No.: 11/266,573

(22) Filed: Nov. 3, 2005

(65) Prior Publication Data

US 2006/0114465 A1    Jun. 1, 2006

Related U.S. Application Data

(60) Provisional application No. 60/624,789, filed on Nov. 3, 2004.

(51) Int. Cl.
*G01N 21/47* (2006.01)

(52) U.S. Cl. ....................... 356/319; 356/446

(58) Field of Classification Search ........ 356/300–334, 356/446
See application file for complete search history.

(56) References Cited

U.S. PATENT DOCUMENTS

| | | | |
|---|---|---|---|
| 4,479,718 A | | 10/1984 | Alman |
| 4,917,495 A | | 4/1990 | Steenhoek |
| 5,387,977 A | * | 2/1995 | Berg et al. .................. 356/407 |
| 5,815,279 A | | 9/1998 | Lex |
| 6,002,488 A | * | 12/1999 | Berg et al. .................. 356/418 |
| 6,198,536 B1 | * | 3/2001 | Baker ......................... 356/402 |
| 2002/0005954 A1 | | 1/2002 | Sperling |
| 2002/0167669 A1 | | 11/2002 | Schwarz |

FOREIGN PATENT DOCUMENTS

| | | | |
|---|---|---|---|
| EP | 0530818 | | 3/1993 |
| EP | 0530818 A2 | * | 10/1993 |
| EP | 1026486 | | 8/2000 |
| JP | 10-010045 | * | 1/1998 |

OTHER PUBLICATIONS

X-Rite MA68 Multi-Angle Spectrophotometer User's Manual, Copyright 1993, X-Rite, Incorporated.*
Pointer, Michael, Nicholas J Barnes, Peter J Clarke and Michael Shaw, A new goniospectrophotometer for measuring goinio-apparent materials, Sep. 27, 2004, Coloration Technology, vol. 121, No. 2, pp. 96-103.*
Partial European Search Report dated Mar. 1, 2006.

* cited by examiner

*Primary Examiner*—Gregory J. Toatley, Jr.
*Assistant Examiner*—Rebecca C. Slomski
(74) *Attorney, Agent, or Firm*—McCarter & English, LLP (57) ABSTRACT

The present disclosure provides for a device, as well as a system and method associated therewith, for, among other things, providing: (i) up to five distinct measurement angles along with an illumination reference channel; (ii) a plurality of illumination sources that provide a focused beam of illumination at specific desired angles of incidence to a sample under target; (iii) a shutter mechanism incorporating a calibration transfer standard; (iv) an internal optical system that is operatively associated with a gimbaled structure suitable to allow vertical and angular conformity to a target sample; and (v) a handheld and operated enclosure incorporating a user interface with a visual display unit complete with interactive navigation means and an activation switch, and a number of surface detecting contact elements operatively associated with the optical system and shutter mechanism.

14 Claims, 13 Drawing Sheets

110 ASPECULAR MEASUREMENT ANGLE

45 DEGREE ILLUMINATION    15 DEGREE ILLUMINATION

FIG. 8C

75 ASPECULAR MEASUREMENT ANGLE

45 DEGREE ILLUMINATION    15 DEGREE ILLUMINATION

FIG. 8D

25 ASPECULAR MEASUREMENT ANGLE

45 DEGREE ILLUMINATION    15 DEGREE ILLUMINATION

FIG. 8E

15 ASPECULAR MEASUREMENT ANGLE

45 DEGREE
ILLUMINATION

15 DEGREE
ILLUMINATION

FIG. 8F

-15 ASPECULAR MEASUREMENT ANGLE

FIG. 8G

45 DEGREE
ILLUMINATION

15 DEGREE
ILLUMINATION

DUAL ILLUMINATION ANGLE GONIOMETRIC SPECTROPHOTOMETER

CROSS-REFERENCE TO RELATED APPLICATIONS

The present application claims the benefit of a now abandoned and commonly assigned provisional patent application entitled "Dual Illumination Angle Goniometric Spectrophotometer", Ser. No. 60/624,789, which was filed on Nov. 3, 2004. The entire contents of the foregoing provisional patent application are hereby incorporated by reference herein.

BACKGROUND

1. Technical Field

The present disclosure relates generally to a device, system and method for optically characterizing a surface. More particularly, the present disclosure relates to a dual illumination angle goniometric spectrophotometer for: (i) providing up to five distinct measurement angles along with an illumination reference channel; (ii) providing a plurality of illumination sources that provide a focused beam of illumination at specific desired angles of incidence to a target sample; (iii) providing a shutter mechanism incorporating a calibration transfer standard; (iv) providing an internal optical system that is operatively associated with a gimbaled structure suitable to allow vertical and angular conformity to a sample under target; and (v) providing a handheld and operated enclosure incorporating a user interface with a visual display unit complete with navigation means and an activation or trigger switch, an internal barcode scanner, a communication interface, a temperature sensor operatively associated with the optical system, and a number of surface detecting contact elements operatively associated with the optical system.

2. Background Art

A surface is goniochromatic if optical measuring quantities associated therewith depend both on the illumination angle and the observation angle of the reflected light when performing a reflection measurement. Such goniochromatic surfaces, which include metallic, pearlescent, lustrous, and/or other special effect surfaces, are used in many different fields in industry, including, for example, the automobile industry in which finishes including a general background of high-gloss paint with reflecting flakes associated therewith so as to effectuate an aesthetic optical effect are commonly utilized. The appearance of these special effect finishes changes dramatically with a change of viewpoint because of the highly directional reflective characteristics of the embedded flakes in so much that such finishes provide a glittering or sparkling optical effect as the eye catches the reflections of different flakes. Goniochromatic surfaces are characterized at the time of manufacture and/or repair in order to provide documentation and to allow for objective comparisons, accurate matching and reliable standardization.

Goniometric measuring devices suitable for characterizing color surfaces are known in the prior art. Consider, for example, the devices and/or methods disclosed in U.S. Pat. Nos. 4,479,718; 4,917,495; 5,387,977 and 5,815,279. Such devices typically illuminate a sample color surface at a fixed angle, via a single light source, and the optical properties (e.g., reflective properties) of such surface are measured from different angles. At least one drawback associated with these conventional devices is found in the less than precise goniometric surface characterization provided by using only a single illumination source and a limited number of measurement angles.

Accordingly, despite that which is known from the prior art, a need remains for a goniometric measuring device having certain desirable features and functionalities. In particular, a need remains for a portable goniometric spectrophotometer suitable for providing at least a dual illumination source for more effectively separating out reflected patterns and multiple measurement angles for detecting such reflected patterns, a shutter mechanism incorporating a calibration transfer standard, an internal optical system that is advantageously associated with an adjusting gimbal-like structure, and a handheld and operated enclosure incorporating a number of advantageous features and capabilities.

These and other advantageous features, functionalities and/or capabilities are provided according to the illustrative aspects associated with the exemplary device, systems/components and/or methods for optically characterizing a surface disclosed herein.

SUMMARY OF THE DISCLOSURE

The disclosed goniometric spectrophotometer of the present disclosure, as well as the various systems/components and/or methods for use associated therewith, have wide-ranging applications in the field of color measurement. In an exemplary application, however, the disclosed device, systems/components and/or methods for optically characterizing a surface may be advantageously utilized to optically characterize surfaces having goniochromatic properties associated therewith.

According to an exemplary embodiment of the present disclosure, a goniometric spectrophotometer includes, in any of a variety of combinations thereof, (i) an ergonomic housing having a user interface with a visual display complete with navigation means and an activation or trigger switch, an internal barcode scanner, a communication (e.g., wireless) interface, a temperature sensor operatively associated with an optical system, and a number of surface detecting contact elements operatively associated with such optical system, (ii) a shutter mechanism incorporating calibration means, (iii) a measuring element operatively associated with the shutter mechanism and including a number of measuring plane detectors; (iii) an optical system operatively associated with a gimbal-like structure suitable to allow vertical and angular conformity to a sample under target; (iv) dual illumination sources for providing a focused beam of illumination at specific desired angles of incidence to the sample under target; and (v) a number of optical measuring elements for providing up to five distinct measurement angles.

For example, one exemplary embodiment of the present disclosure includes a portable goniometric spectrophotometer having a housing; a user interface incorporated with the housing; a shutter mechanism; an optical system in optical communication with the shutter mechanism; and a power source operably coupled to the shutter mechanism and optical system.

In another exemplary embodiment, a method of using a portable goniometric spectrophotometer is disclosed. The method includes establishing a calibration transfer standard for the optical system by supporting a measuring interface thereof on a calibration tile inside a housing. Then turning an actuating element in a first direction to open an ingress/egress aperture thus opening shutter elements cooperating to close the ingress/egress aperture. Further turning of the actuating element selectively exposes and projects the measuring interface of the optical system from the housing a predefined distance. The target sample is then contacted with the measuring interface so as to define a measuring plane that is orthogonal to the axis of measurement.

In yet another embodiment, a portable dual illumination angle goniometric spectrophotometer system is disclosed. The system includes an ergonomic handheld and operated enclosure incorporating a user interface with a visual display complete with navigation means and an activation switch; an internal barcode scanner; a wireless communication interface; a temperature sensor operatively associated with an optical system; and a plurality of measuring plane detectors operatively associated with the optical system.

Additional structural features and operational functionalities associated with the goniometric spectrophotometer, as well as systems and methods associated therewith according to the present disclosure will be apparent from the detailed description and schematic illustrations which follow, particularly when read and reviewed by a person of skill in the relevant art.

BRIEF DESCRIPTION OF THE DRAWINGS

Structural and functional aspects, features, and advantages of the present disclosure will be understood and the manner of making and using such structures will become more readily apparent when the following description is reviewed by persons skilled in the art in conjunction with the accompanying drawings, wherein.

DETAILED DESCRIPTION OF EXEMPLARY EMBODIMENTS

As noted above, the present disclosure provides for a device, as well as a system and method associated therewith, for, among other things, providing: (i) up to five distinct measurement angles along with an illumination reference channel; (ii) a plurality of illumination sources that provide a focused beam of illumination at specific desired angles of incidence to a sample under target; (iii) a shutter mechanism incorporating a calibration transfer standard; (iv) an internal optical system that is operatively associated with a gimbaled structure suitable to allow vertical and angular conformity to a target sample; and (v) a handheld and operated enclosure incorporating a user interface with a visual display unit complete with interactive navigation means and an activation or trigger switch, an internal barcode scanner, a communication interface, a temperature sensor operatively associated with the optical system, and a number of surface detecting contact elements operatively associated with the optical system and shutter mechanism. An exemplary goniometric spectrophotometer incorporating at least the foregoing advantageous structural features and operational functionalities is described below.

The disclosed illustrative goniometric spectrophotometer has wide ranging color measurement utility. Thus, for example, the disclosed goniometric spectrophotometer may be advantageously employed to make color measurements with respect to any of a variety of fabrics, plastics and/or paint samples. In use, a sample is positioned adjacent a measuring foot or interface associated with the goniometric spectrophotometer. The spectral response characteristics for the sample is preferably obtained by projecting light from a number of illumination sources (e.g., two or more) toward the sample, and color information is captured through light gathering optics positioned at diverse angles so as to measure the light reflected from the sample and thereby define the optical characteristics associated with color materials, including sophisticated colors such as metallic, pearlescent, lustrous, and/or other special effect paints, with relatively high accuracy and repeatability. A color spectrum analysis can be effected and color values calculated, e.g., by an appropriately programmed micro-processor.

Figure 1:
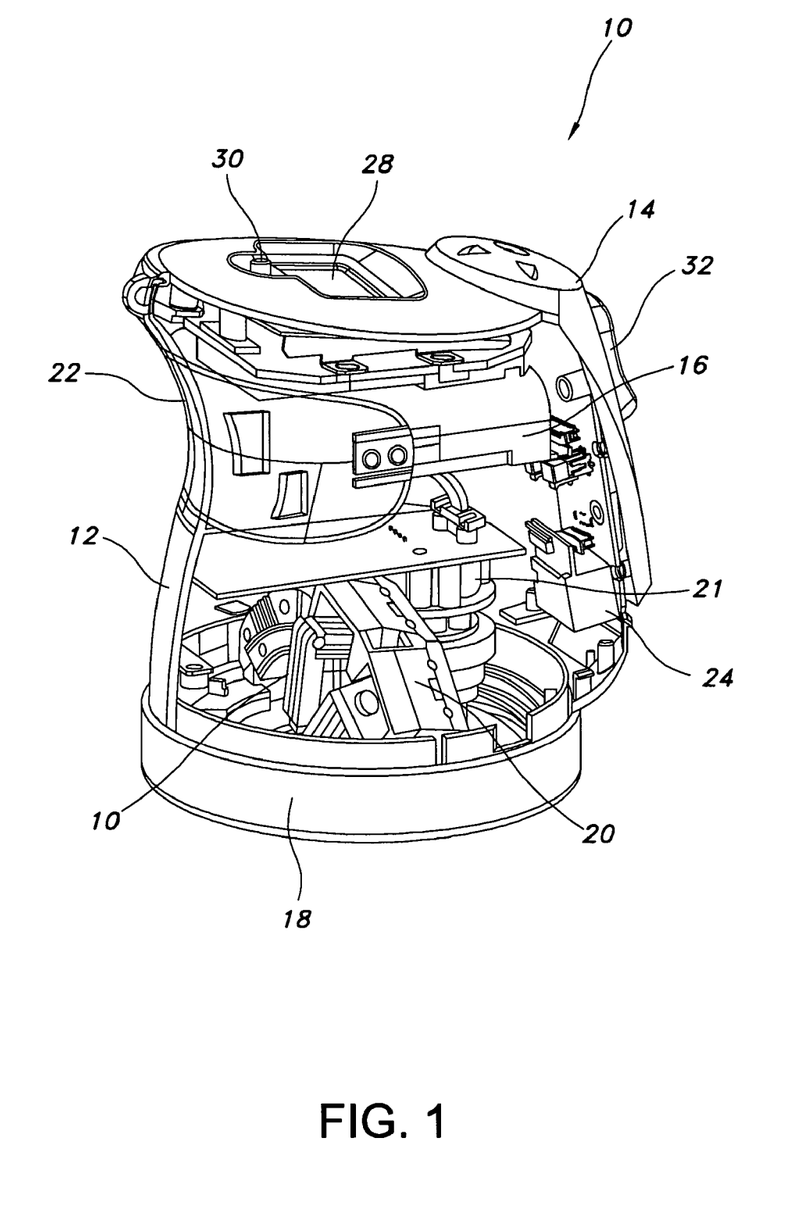
FIG. 1 is a partially-sectional perspective view of an exemplary goniometric spectrophotometer according to the present disclosure.
Figure 2:
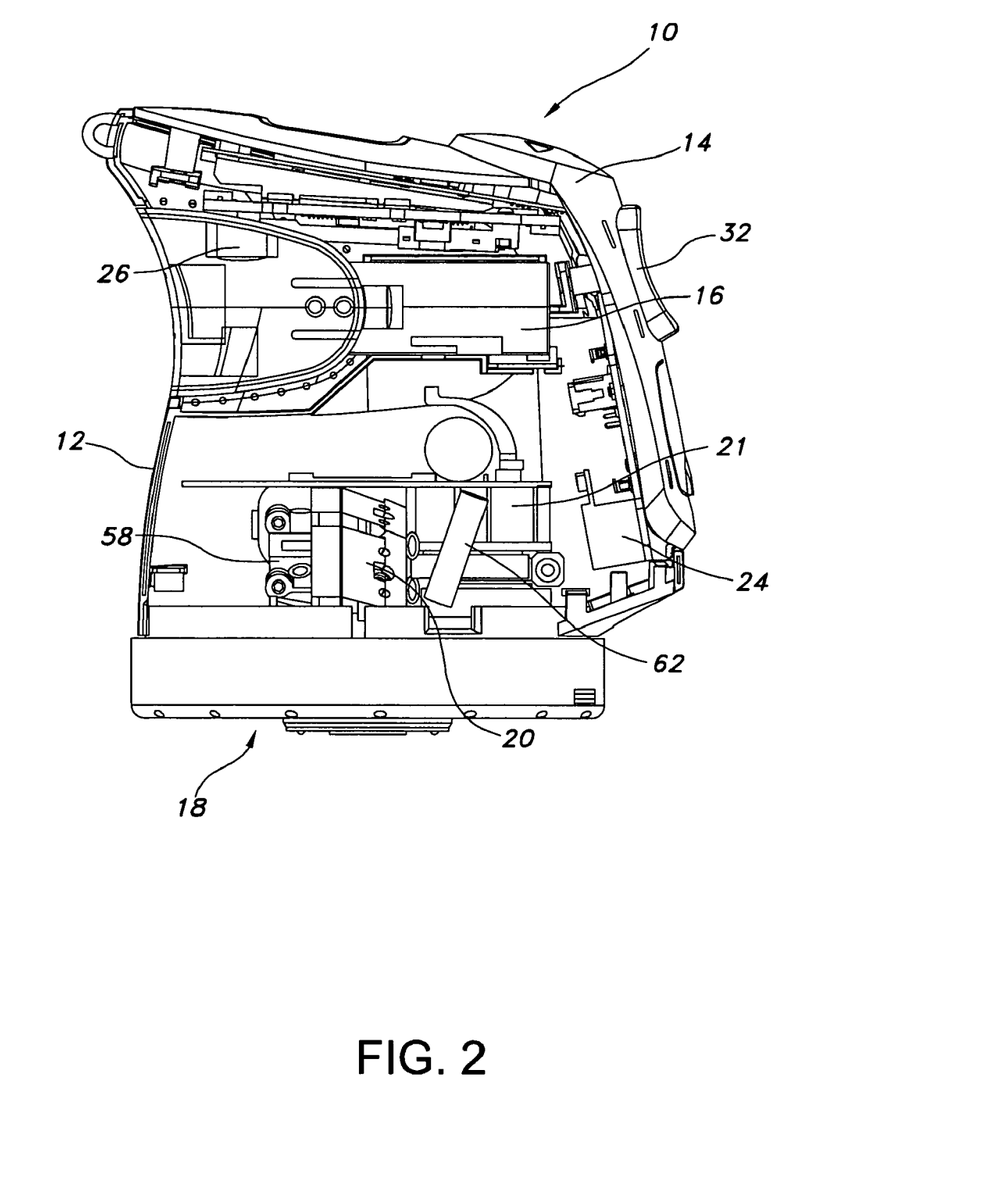
FIG. 2 is a partially-sectional side view of the exemplary goniometric spectrophotometer of FIG. 1.
Figure 3:
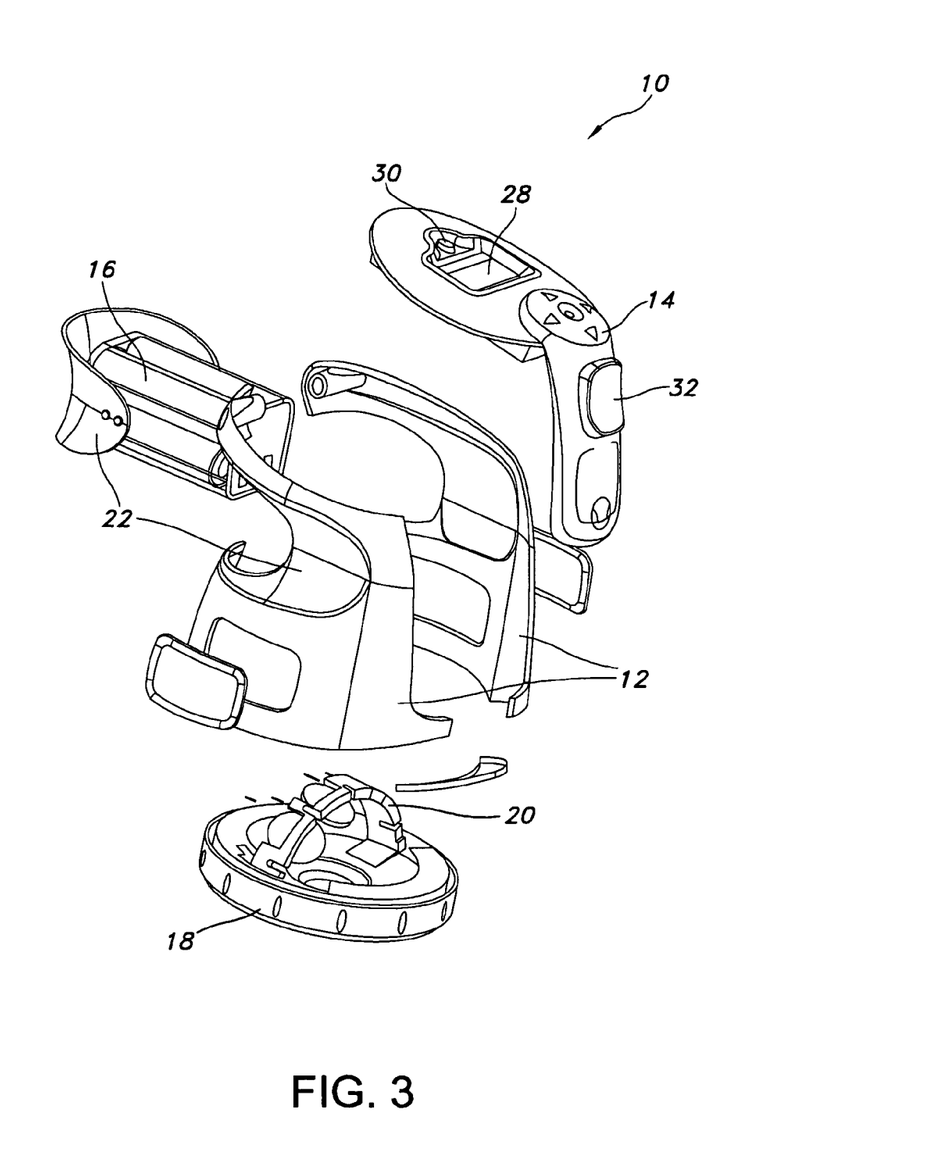
FIG. 3 is an exploded perspective view of the exemplary goniometric spectrophotometer of FIG. 1.

With reference to FIGS. 1-3, a portable goniometric spectrophotometer 10 incorporating advantageous features according to an exemplary embodiment of the present disclosure is depicted. Goniometric spectrophotometer 10, as shown, includes at least a housing 12 adapted to accommodate a variety of advantageous features and/or components associated with the goniometric spectrophotometer 10, a user interface 14, a power source 16, a shutter mechanism 18 and an optical system 20.

The housing 12, in a preferred aspect of the present disclosure, is a composite structure suitable to enable a user to effectively and efficiently hold, manage, transport, stow and/or otherwise manipulate the goniometric spectrophotometer 10. The housing, as shown, defines an ergonomic handle 22 shaped to facilitate intuitive and comfortable handling of the goniometric spectrophotometer 10. The user interface 14, power source 16, shutter mechanism 18 and optical system 20 are operatively associated with the housing 12 so as to be readily available to the user as appropriate. In addition, the housing 12 may incorporate a number of additional and/or alternative features, including for example, an internal scanner 24 (e.g., a laser barcode scanner) to, for instance, facilitate comparing and/or matching a sample to a commercially available product, or a communication interface 26 (e.g., wireless or wired) to, for instance, facilitate transmitting and/or receiving data from external devices (e.g., computers and the like).

With particular reference to FIG. 3, the user interface 14, in a preferred aspect of the present disclosure, includes a visual display 28, such as an LCD or LED display panel, complete with a multi-directional navigation control 30 suitable to provide the user with intuitive means for interacting with the goniometric spectrophotometer 10. Additionally, as shown, the user interface 14 preferably includes a trigger switch 32 suitable for the purpose of activating and/or deactivating the goniometric spectrophotometer 10 as desired. Furthermore, as will be readily apparent to those skilled in the pertinent art, in other aspects of the present disclosure, not shown, additional and/or alternative interfacing means (e.g., a keypad) equally may be provided.

With further reference to FIG. 3, the goniometric spectrophotometer 10 preferably includes a power source 16 such as, for example, one or more conventional rechargeable and/or replaceable batteries suitable for the purpose of providing DC power to the goniometric spectrophotometer 10 as well as any of the components thereof as appropriate. Alternatively, or in addition, an AC adapter input, not shown, may be provided for the purpose of powering the goniometric spectrophotometer 10 and appropriate components thereof with conventional external AC power.

Figure 4:
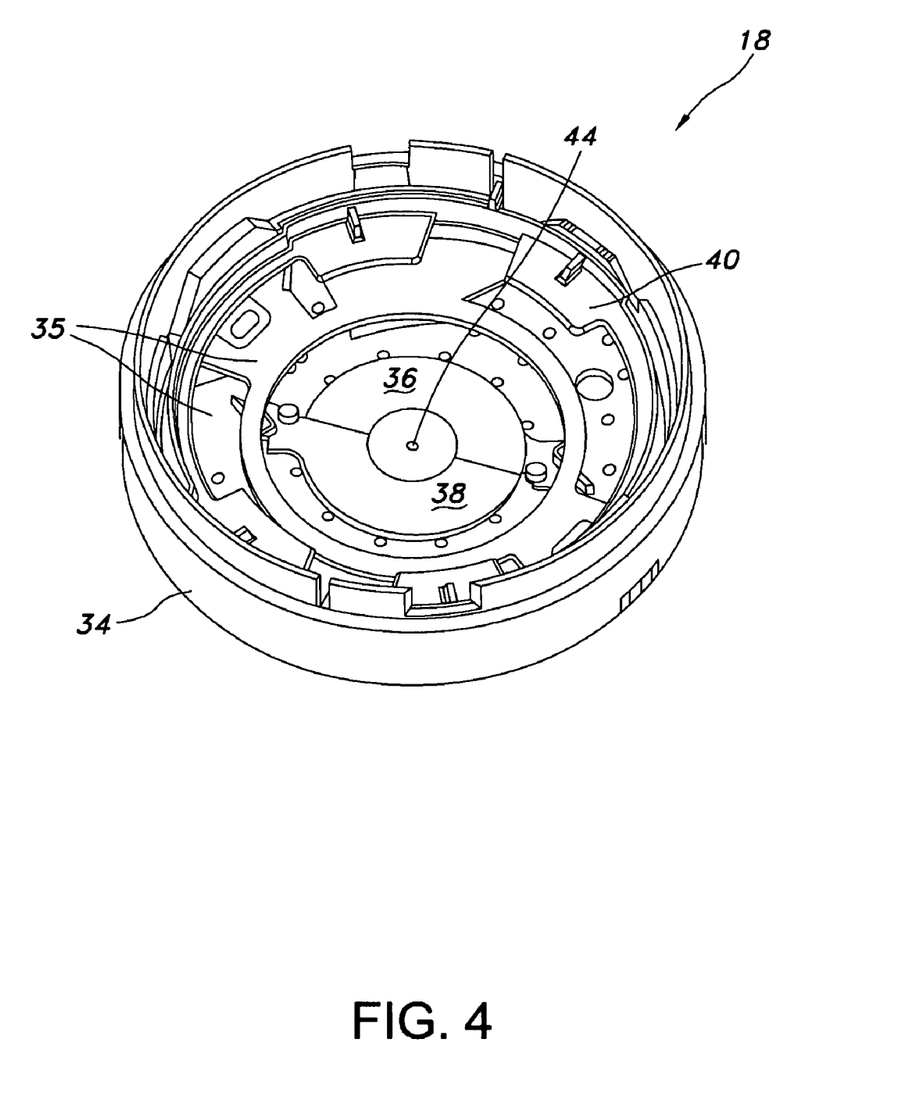
FIG. 4 is a schematic perspective top view of an exemplary shutter mechanism according to the present disclosure.
Figure 5:
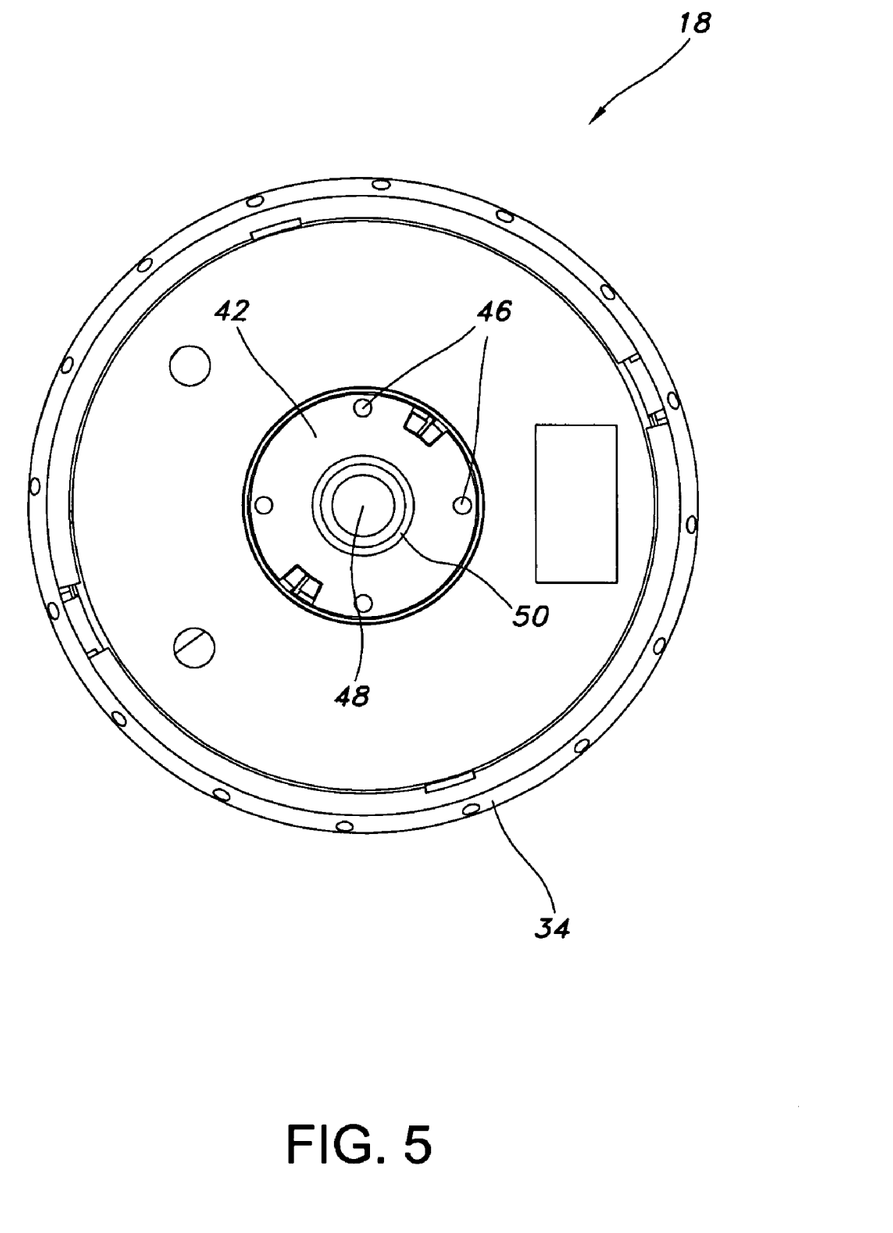
FIG. 5 is a schematic bottom plan view of the exemplary shutter mechanism of FIG. 4.

Turning to FIGS. 4 and 5, an exemplary shutter mechanism 18 is depicted according to the present disclosure. As shown, the shutter mechanism 18 includes an actuating element 34 for activating and controlling the shutter mechanism 18. The actuating element 34, as shown, is a rotating member operatively associated with a cam mechanism 35. The cam mechanism 35, in turn, is operatively associated with both a pair of shutter elements 36, 38 and a suspension element 40.

The shutter elements 36, 38 operatively move with respect to each other so as to selectively expose a measuring interface 42 associated with the optical system 20. At least one of the shutter elements 36, 38 has a calibration tile 44 (FIG. 4) integrally associated therewith so as to provide internal calibration means. The calibration tile 44 is adapted to define a calibration position at which the measuring interface 42 is preferably positioned in an inoperative state.

The suspension element 40 accommodates the optical system 20 so as to enable the measuring interface 42, which, in an inoperative state, is enclosed within the housing 12, to extend or project from the housing 12 so as to make contact with a target sample via a number of contacting elements 46. As three or more of these contacting elements 46 interact with a surface of the sample so as to be depressed, a measuring plane is defined which is orthogonal to the axis of measurement. Illumination beams 48 illuminate the sample and multiple measurement beams 50 measure the light reflected from the surface of the sample.

Figure 6A:
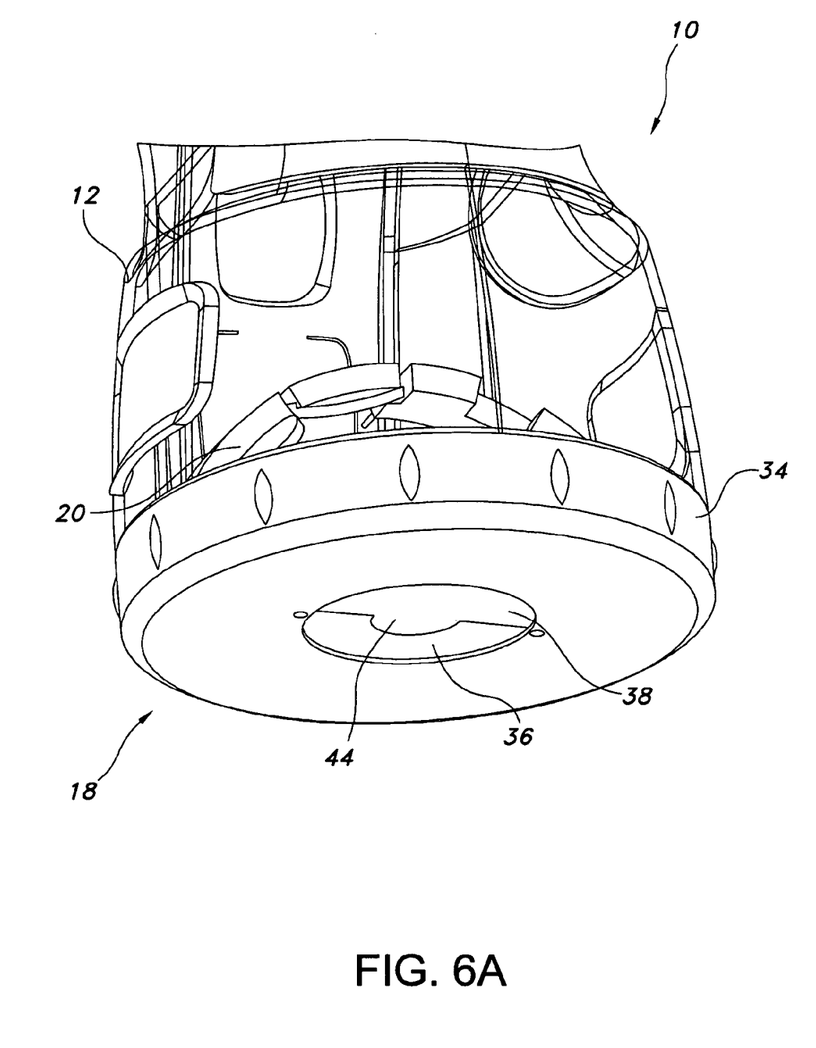
FIGS. 6a-6d are schematic perspective views of the shutter mechanism schematically depicted in FIGS. 4 and 5, demonstrating additional illustrative operative states thereof.
Figure 6B:
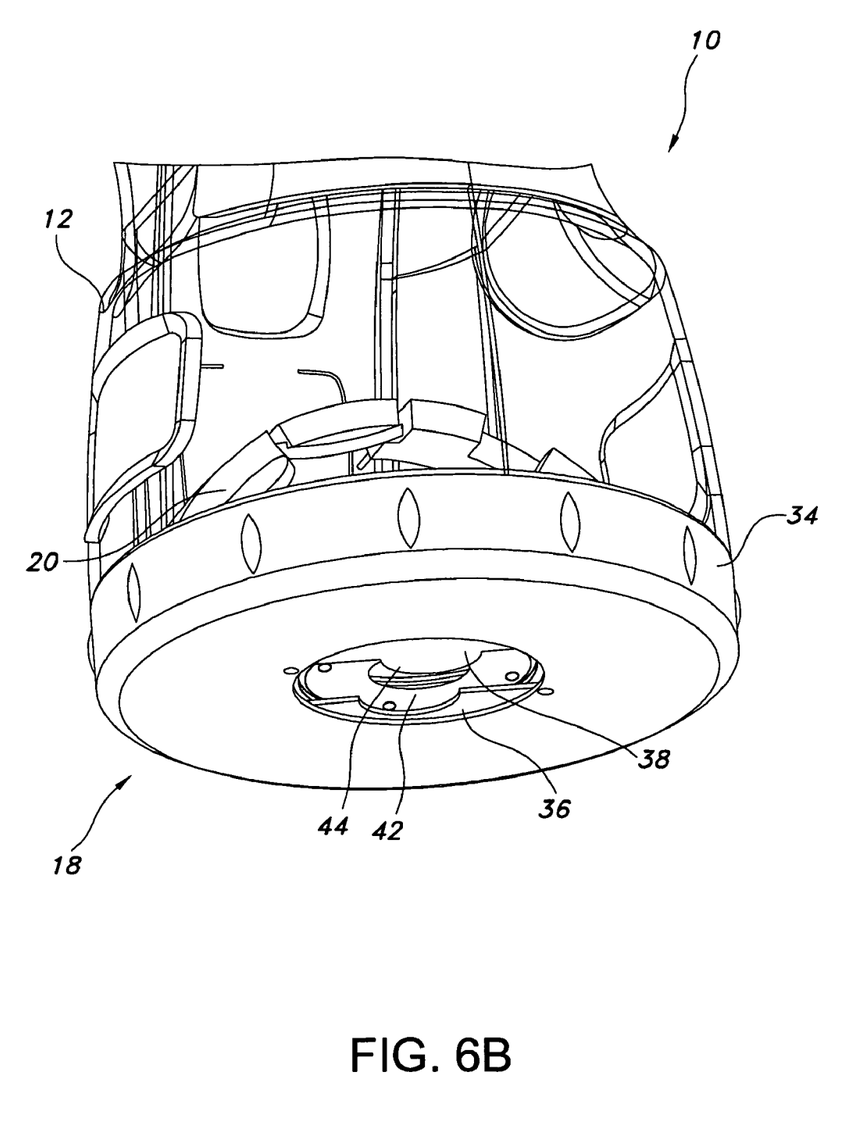
Figure 6C:
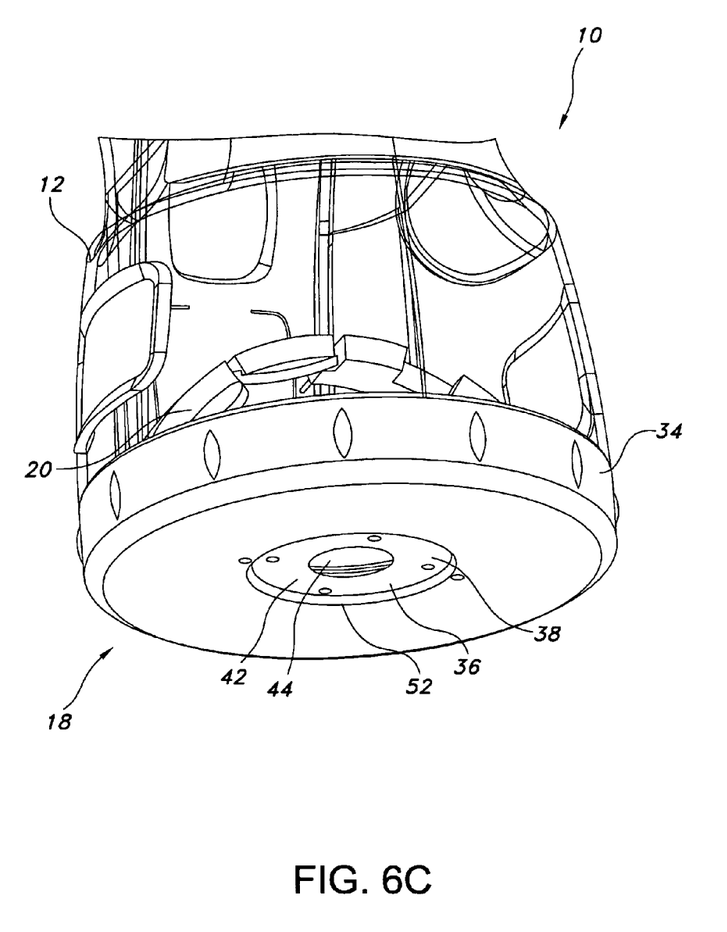
Figure 6D:
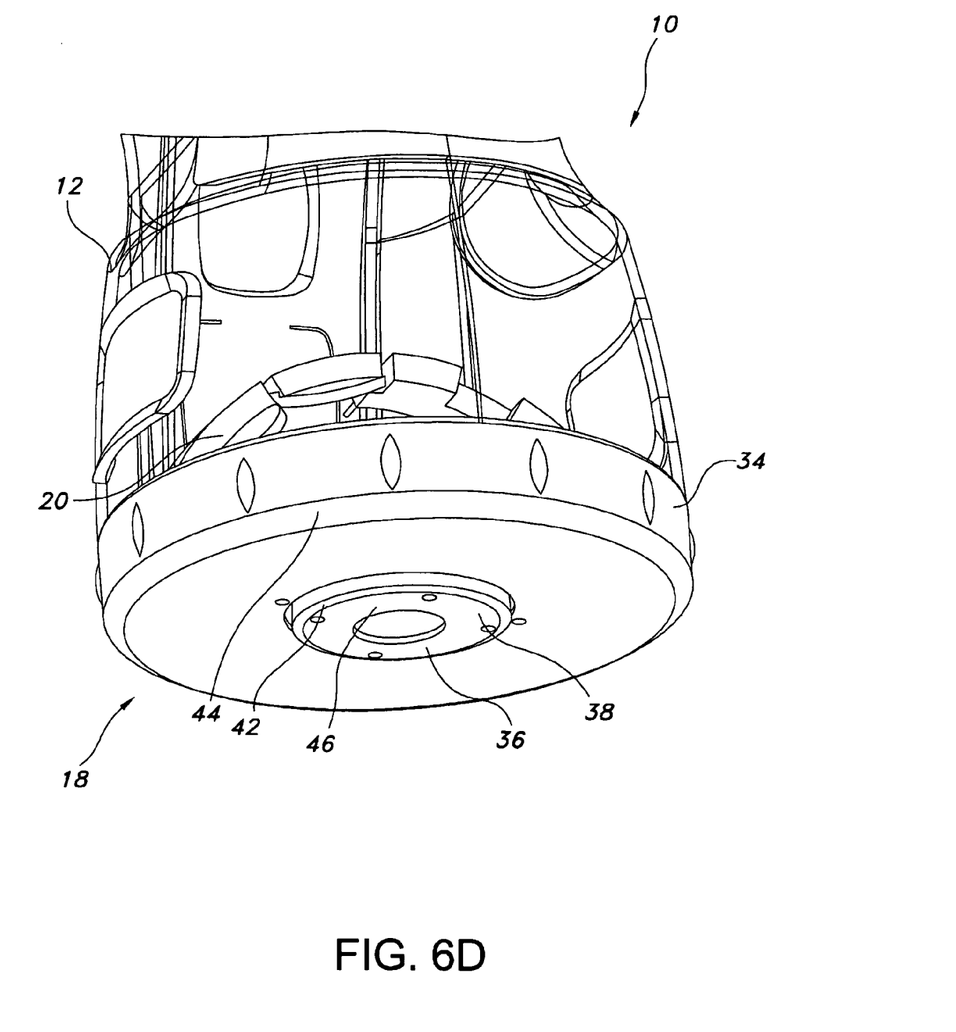

Having identified and described various preferred features of the exemplary shutter mechanism 18, the operation of such shutter mechanism will now be discussed with reference to FIGS. 6a-6d. FIG. 6a is an enlarged perspective view showing the lower portion of the goniometric spectrophotometer 10, which portion is intended for interacting with a target sample. As shown, the shutter elements 36, 38 are cooperating to close an ingress/egress aperture 52 (FIG. 6c) suitable for allowing the measuring interface 42 of the optical system 20 to be selectively exposed. In this closed state, the calibration tile 44 supports the measuring interface 42 so as to establish a calibration transfer standard. As shown in FIG. 6b, to expose the measuring interface 42 of the optical assembly, the actuating element 34 is rotated in a first direction. This rotation of the actuating element 34, as shown, causes the shutter elements 36, 38 to move relative to each other so as to open the ingress/egress aperture 52 (FIG. 6c). The actuating element 34 rotates to a first position shown in FIG. 6c wherein the shutter elements 36, 38 are separated so that the ingress/egress opening is completely open. Continued rotation of the actuating element 34 in the first direction causes the optical system 20 to move so that the measuring interface 42 thereof projects from the housing 12 a predefined distance such as is shown in FIG. 6d. It is in this state that the measuring interface 42, via the contacting elements 46 thereof, interacts with the target sample surface so as to define a measuring plane that is orthogonal to the axis of measurement. As desired, the actuating element 34 may be rotated in a second direction, opposite to the first direction, to cause the measuring interface 42 to withdraw back into the housing as shown in FIG. 6c and cause the shutter elements 36, 38 to move toward each other as shown in FIG. 6b resulting in the ingress/egress aperture 52 being closed once again as shown in FIG. 6a. Once the ingress/egress opening is properly closed, continued rotation of the actuating element 34 in the second direction causes the measuring interface 42 to come into contact with the calibration tile 44 so as to be supported thereby during non-use.

From the foregoing, it will be readily apparent to those skilled in the pertinent art that the advantageous structures associated with the exemplary shutter mechanism disclosed herein may be modified, in whole or in part, as may be desired to achieve specific design and/or operational objectives and/or requirements without departing from the scope of the present disclosure.

Figure 7:
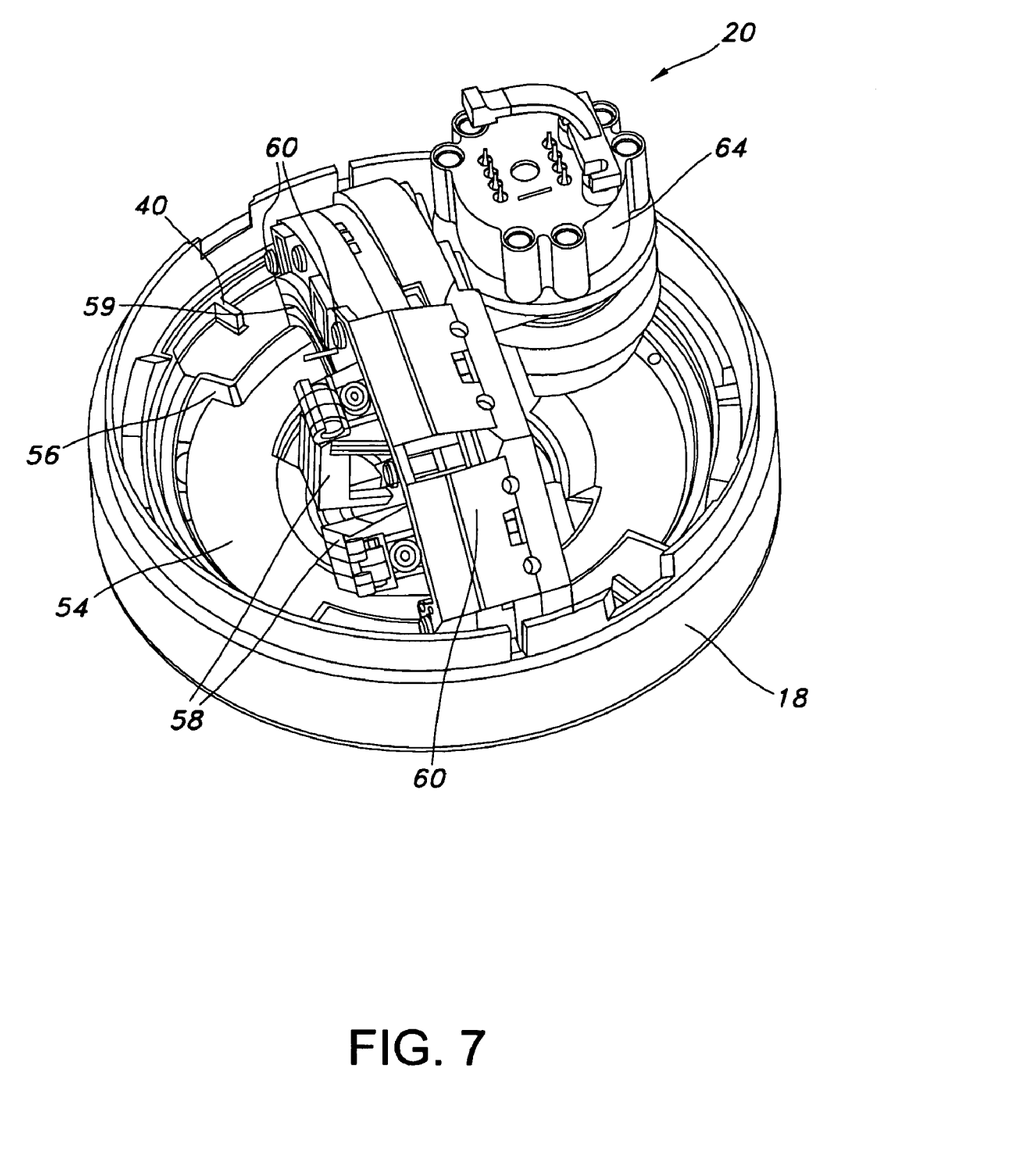
FIG. 7 is a schematic perspective top view of an exemplary optical system according to the present disclosure.

Turning now to FIG. 7, an exemplary optical system 20 is depicted according to the present disclosure. As shown, the optical system 20 is operatively associated with the shutter mechanism 18 via the suspension element 40, an optical support or base member 54 and one or more elastomeric elements 56 located between the suspension element 40 and the optical base member 54. The suspension element 40 and the optical base member 54 cooperate, via the elastomeric elements 56, to effectuate an adjusting gimbal-like structure that allows the optical system 20, including the measuring interface 42 thereof, to freely move within the housing 12 (demonstrated in FIGS. 6a-6d). This freedom of motion enables the measuring interface 42 to effectively interact with different sample surfaces, including curved surfaces, so that a measurement plane can be established via the contacting elements 46. In a preferred aspect of the present disclosure, the measuring interface 42 and/or the optical system 20 has at least three degrees of freedom with respect to motion. That is, the measuring interface 42 and/or the optical system 20 can move up and down (e.g., approx. 2 mm), can tilt up and down (e.g., approx. 3°), and can tilt side to side (e.g., approx. 3°). As will be readily apparent to those skilled in the pertinent art, the measuring interface 42 and/or optical system 20 can be provided with additional degrees of freedom as needed to effectuate different operations.

With continued reference to FIG. 7, the optical system 20 is positioned above the shutter mechanism 18. The optical system 20 includes multiple light sources for projecting light on a sample in such a manner so at to more effectively separate out the various incidence angles associated with surfaces having special effect or interference pigments (e.g., metallic, pearlescent, etc.). In a preferred aspect of the present disclosure, a dual illumination source 58 is employed. The dual illumination source 58 is preferably adapted so as to focus the illumination beams and thereby inhibit any stray light interference. In addition, a dual light trap assembly 59 can be operatively connected to the optical system 20 preferably being positioned at the specular reflection angle relative to the dual illumination source 58. The light trap assembly 59 further reduces the possibility of stray light interference on highly reflective samples. The optical system 20 also includes a number of optical measuring elements 60 (e.g., a series of optical fibers) positioned at predetermined locations relative to the dual illumination source 58 so as to define up to five distinct measurement angles. In a preferred aspect of the present disclosure, these optical measuring elements 60 operate to receive the reflected light waves emanating from the surface of the target sample. Thus, the optical system 20 is suitable for measuring spectral reflectance properties of a sample placed in front of the dual illumination source 58 and multiple measuring elements 60 thereof and, in a preferred aspect of the present disclosure, the optical system 20 is configured for separating out incident angles while simultaneously providing multi-angle measurement functionality. As will be readily apparent to those skilled in the pertinent art from the present disclosure, the optical system 20 may have any of a variety of additional components and/or features associated therewith in order to advance the effective operation of the exemplary goniometric spectrophotometer of the present disclosure. For example, the optical system, as clearly shown in FIG. 2, may include a sample area temperature sensor 62, as well as a multi-channel analyzer 64.

Referring to FIGS. 8a-8g, the illumination and measurement angle tolerances associated with the optical system 20 are depicted. In a preferred aspect of the present disclosure, an illumination beam cone angle is specifically controlled to allow for the tightest measurement angle tolerance and reduce or minimize the effects of channel saturation. The determination of the exemplary angles dimensioned in the diagrams result from projecting the cone angle defined by a numerical aperture (e.g., 0.22) associated with a measurement fiber (e.g., measuring element 60) onto an illuminated sample area as demonstrated in FIG. 8a so as to give a total acceptance angle of approximately 25°.

Figure 8A:
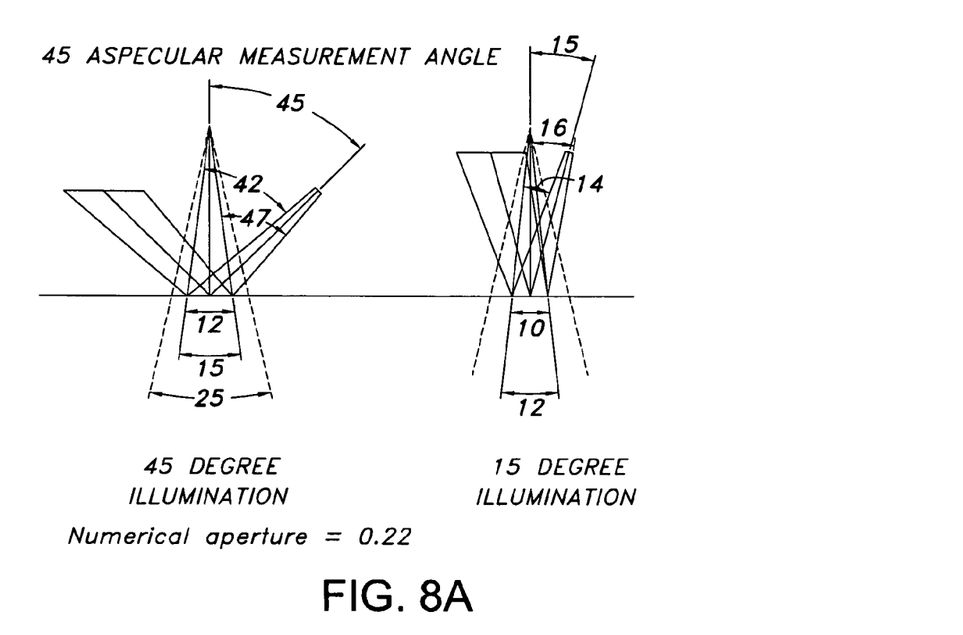
FIGS. 8a-8g are schematic diagrams of exemplary illumination and measurement angle tolerances according to the present disclosure.

For the exemplary 45:90 and 75:90 configurations shown in FIG. 8a, the theoretical illumination beam uniformity for a 45° illumination angle is about 8% across the aperture while that of a 15° illumination angle is about 3%. An additional elliptical aperture is utilized to control the circular beam profile for the 45° illumination, whereas the circular beam profile of the 15° illumination profile does not require such an additional aperture. Due to the controlled nature of the illumination cone angle, the illuminated sample area is a subset of the area of view defined by the numerical aperture of the measurement fiber. Thus, as provided in both the American Society of Testing and Materials (ASTM) E2194-03 and WK1164 standard, the angle dimensions extend from the outer diameter of the measurement fiber to the extent of the illumination spot profile. In the case of the 45° illumination where the beam profile is slightly elliptical, the major diameter defines the extent of the illumination spot profile.

The plus/minus angle tolerance for the 45° aspecular measurement angle of FIG. 8a is +2° and -3° respectively. Hence, the total angular tolerance spread of 5° is substantially less than the 16° allowed by the ASTM E2194-03 and WK1164 standard. In addition, the plus/minus angle tolerance for 15° aspecular measurement angle, achieved using the 15° illumination source, is +1° and -1° respectively. Thus, the total angular tolerance spread of 2° is also substantially less than the 16° allowed by the above-noted standard.

Figure 8B:
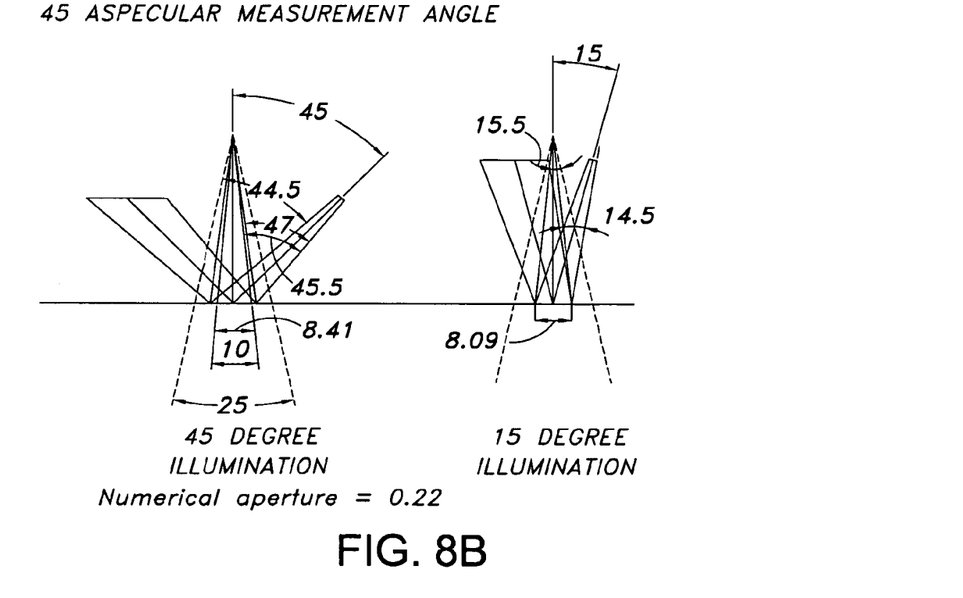

With reference to FIG. 8b, the "fill factor" or the value resulting from an area of view calculation which is used to approximate the percentage of rays within a 0.5° boundary of the nominal receiver angle. This approximation is used due to the less than 10% intensity variation over the illuminated sample area. A simple ratio calculation (i.e., the elliptical area of the view of the fiber at the ±0.5° tolerance divided by the total elliptical area of view of the illuminated sample area) is used to make this approximation. Accordingly, using the major diameter of the measurement ellipse defined by the ±0.5° criteria as outlined in the ASTM E2194-03 and WK1164 standard, the fill factor for the 45:90 configuration is about 70%, which is substantially higher than the minimum requirement of 10% prescribed by the ASTM E2194-03 and WK1164 standard. Likewise, the fill factor value for the 75:90 configuration, i.e., about 81%, is substantially higher than the ASTM E2194-03 and WK1164 prescribed standard of 13%.

Figure 8C:
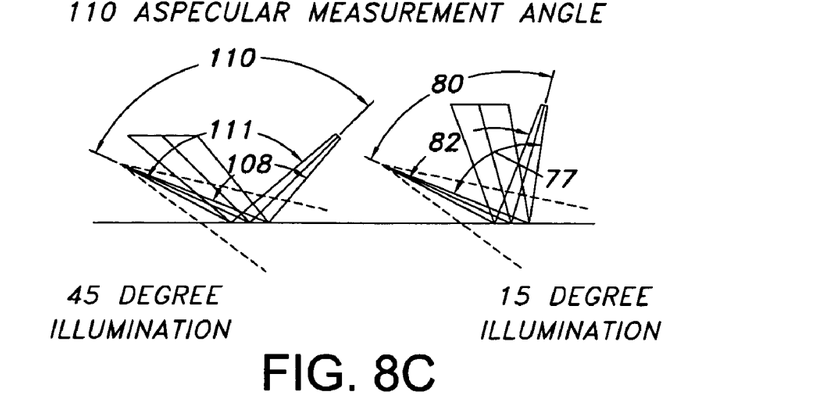

With reference to FIG. 8c, the plus/minus angle tolerance for a 110° aspecular measurement angle is +1° and -2° respectively. Thus, the total angular tolerance spread of 3° is substantially less than the 34° allowed by the ASTM E2194-03 and WK1164 standard. In addition, the fill factor for the 45:25 configuration is 100% well above the minimum requirement of 5% established by the ASTM E2194-03 and WK1164 standard.

Figure 8D:
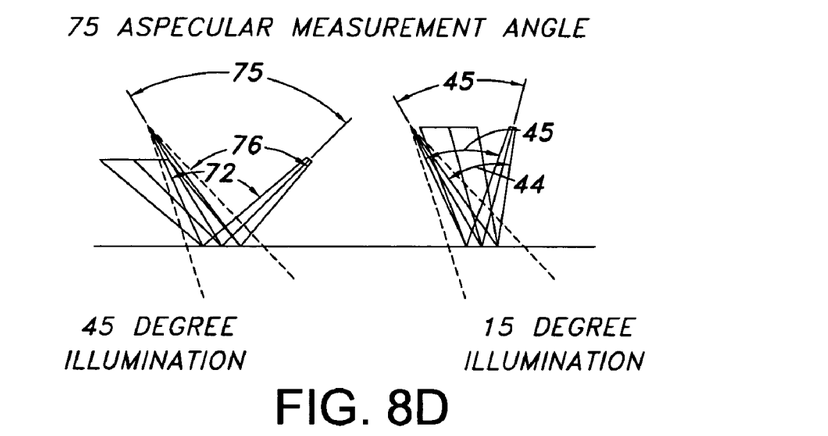

With reference to FIG. 8d, the plus/minus angle tolerance for a 75° aspecular measurement angle is +1° and -3° respectively. Therefore, the total angular tolerance spread of 4° is substantially less than the 20° prescribed by the ASTM E2194-03 and WK1164 standard. A redundant 45° aspecular angle is achieved using the 15° illuminating source and the plus/minus angle tolerance for this 75:60 configuration is +0° and -1° respectively so as to define a total angular tolerance spread of 1°. Additionally, the fill factor for the 45:60 configuration is calculated to be about 66%, which is notably higher than the 10% prescribed by the ASTM E2194-03 and WK1164 standard.

Figure 8E:
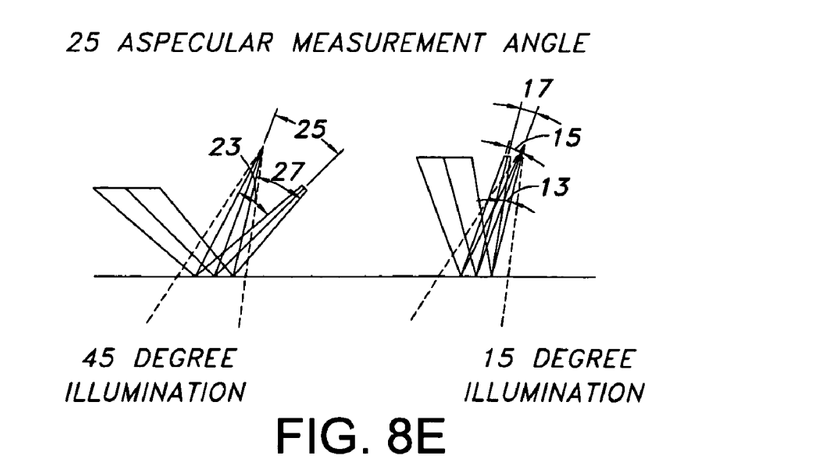

Turning to FIG. 8e, the plus/minus angle tolerance for a 25° aspecular measurement angle is ±2° for a total angular tolerance spread of 4° as compared to the 16° prescribed by the ASTM E2194-03 and WK1164 standard. The 5° aspecular angle may cause channel saturation unless mechanically shuttered. The fill factor for the 75:110 configuration is calculated to be about 60%, a significantly higher value than the 15% outlined in the ASTM E2194-03 and WK1164 standard.

Figure 8F:
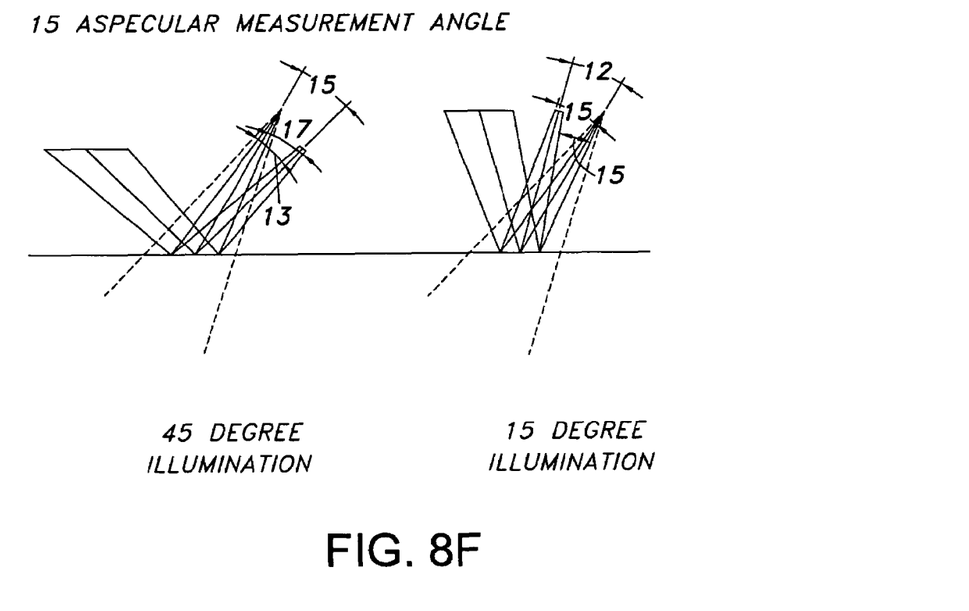

Referring to FIG. 8f, the plus/minus angle tolerance for a 15° aspecular measurement angle, similar to the 25° aspecular measurement angle, is ±2° for a total angular tolerance spread of 4° as compared to the 16° prescribed by the ASTM E2194-03 and WK1164 standard. A -15° aspecular angle can be achieved using the 15° illumination source and the plus/minus angle tolerance for this 75:120 configuration is ±0° for a total angular tolerance spread of 0° in comparison to the 16° allowed by the ASTM E2194-03 and WK1164 standard. Also, the fill factor value for the 75:120 configuration is about 100%. In addition, the fill factor value for the 45:120 configuration is about 65%, which is well above the minimum of 13% required by the ASTM E2194-03 and WK1164 standard.

Figure 8G:
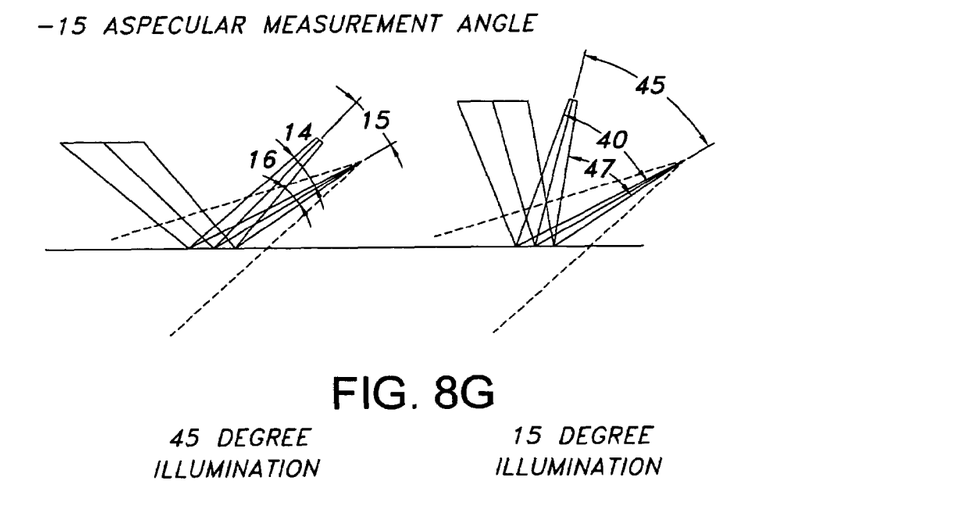

Referring to FIG. 8g, the plus/minus angle tolerance for a -15° aspecular measurement angle, similar to the 25° aspecular measurement angle, is ±1° for a total angular tolerance spread of 2° as compared to the 16° prescribed by the ASTM E2194-03 and WK1164 standard. A -45° aspecular angle can be achieved using the 15° illumination source such that the plus/minus angle tolerance for this 75:150 configuration is ±2° for a total angular tolerance spread of 4°. Also, the fill factor value for the 75:120 configuration is about 100%. In addition, the fill factor value for both the 45:150 and the 75:150 configurations is about 100%.

Thus, in a preferred aspect of the present disclosure, the goniometric spectrophotometer 10 employs an illumination optical system having inherent characteristics of providing a minimized angular deviation with respect to various nominal aspecular angles as outlined in both the ASTM E2194-03 and WK1164 standard. The optical system 20 associated with the goniometric spectrophotometer 10, accordingly, provides a very uniform illumination area and through the use of optical fiber detection at each aspecular angle with a large portion of the aspecular rays for each case meets the ±0.5° criteria prescribed in both the ASTM E2194-03 and WK1164 standard.

Although the present disclosure has been provided with reference to exemplary embodiments thereof, the present disclosure is not to be limited thereto. Rather, modifications, enhancements and/or variations to the disclosed devices, systems and features are contemplated, and such modifications, enhancements and/or variations will not depart from the spirit or scope of the present disclosure. Moreover, it is specifically contemplated that any one or more of the disclosed exemplary structures may be employed in a goniochromatic application, but that it is not necessary that all such structures be implemented to realize the benefits associated with each structure individually. Thus, persons of skill in the art will understand that the advantageous structures disclosed herein may be employed, in whole or in part, as may be desired to achieve specific design and/or operational objectives and/or requirements.

What is claimed is:

1. A goniometric spectrophotometer comprising:
   a housing;
   a user interface incorporated with the housing;
   a shutter mechanism operatively associated with the housing;
   an optical system in optical communication with the shutter mechanism and including a measuring interface; and
   a power source operably coupled to the shutter mechanism and optical system;
   wherein the optical system provides at least five distinct measurement angles alone with an illumination reference channel and includes a plurality of illumination sources;
   the shutter mechanism includes an actuating element for activating and controlling the shutter mechanism;
   the actuating element is a rotating member operatively associated with a cam mechanism, which in turn, is operatively associated with both a pair of shutter elements and a suspension element; and
   the suspension element accommodates the optical system so as to enable the measuring interface, which, in an inoperative state, is enclosed within the housing, to extend or project from the housing so as to make contact with a target sample via three or more contacting elements.

2. The goniometric spectrophotometer of claim 1, wherein the three or more contacting elements interact with a surface of the sample so as to be depressed, and a measuring plane is defined which is orthogonal to an axis of measurement.

3. A goniometric spectrophotometer comprising:
   a housing;
   a user interface incorporated with the housing;
   a shutter mechanism operatively associated with the housing;
   an optical system operatively associated with the housing and in optical communication with the shutter mechanism, the optical system including a measuring interface; and
   a power source operably coupled to the shutter mechanism and optical system;
   wherein the optical system provides at least five distinct measurement angles along with an illumination reference channel and includes a plurality of illumination sources; and
   further comprising a suspension element operatively associated with the measuring interface of the optical system to effectuate an adjusting gimbal-like structure allowing the optical system, including the measuring interface thereof, to freely move within the housing.

4. The goniometric spectrophotometer of claim 3, wherein the suspension element includes a plurality of elastomeric elements providing three degrees of freedom of movement of the measuring interface so that a measurement plane can be established via three contacting elements protruding from the measuring plane.

5. The goniometric spectrophotometer of claim 4, wherein the measuring interface is movable up and down in a range of about 2 mm, tiltable up and down about 3°, and tiltable side to side about 3°.

6. A method of using a goniometric spectrophotometer, the method comprising:
   establishing a calibration transfer standard for an optical system by supporting a measuring interface thereof on a calibration tile inside a housing;
   turning an actuating element in a first direction to open an ingress/egress aperture thus opening shutter elements cooperating to close the ingress/egress aperture;
   further turning of the actuating element to selectively expose and project the measuring interface of the optical system from the housing a predefined distance; and
   contacting a target sample with the measuring interface so as to define a measuring plane that is orthogonal to an axis of measurement.

7. The method of claim 6, further comprising:
   turning the actuating element in a second direction, opposite to the first direction, to cause the measuring interface to withdraw back into the housing and cause the shutter elements to move toward each other; and
   further turning the actuating element in the second direction once the ingress/egress opening is closed causing the measuring interface to come into contact with the calibration tile so as to be supported thereby during non-use.

8. A goniometric spectrophotometer comprising:
   a housing;
   a shutter mechanism operatively associated with the housing; and
   an optical system in optical communication with the shutter mechanism and including a measuring interface;
   wherein the shutter mechanism includes an actuating element selectively actuatable for opening an aperture to the housing, and for projecting the measuring interface, which, in an inoperative state, is enclosed within the housing, outward of the housing via the aperture for purposes of contacting a target sample with the measuring interface.

9. The goniometric spectrophotometer of claim 8, wherein the shutter mechanism further includes a shutter element for closing the aperture, and wherein the actuating element is selectively actuatable for opening the aperture by moving the shutter element relative to the aperture.

10. The goniometric spectrophotometer of claim 8, wherein the measuring interface includes at least three contacting elements for contacting the target sample, and wherein the measuring interface is further operable to define a measurement plane orthogonal to an axis of measurement by contacting the target sample via the at least three contacting elements.

11. The goniometric spectrophotometer of claim 8, further comprising a suspension element for accommodating the optical system, the suspension element including a gimbal-like structure for enabling the measuring interface to rotate relative to the housing and thereby achieve an angular conformity relative to the target sample.

12. A method of using a goniometric spectrophotometer, the method comprising:
    enclosing a measuring interface of an optical system within a housing when the measuring interface is in an inoperable state; and
    deploying the measuring interface, the deploying step including projecting the measuring interface outward of the housing toward a target sample for purposes of contacting the target sample with the measuring interface.

13. The method of claim 12, wherein the step of deploying the measuring interface includes selectively actuating an actuating element for opening an aperture to the housing and projecting the measuring interface outward of the housing via the aperture.

14. The method of claim 12, wherein the step of deploying the measuring interface includes selectively actuating an actuating element for exposing the measuring interface by displacing a shutter, the shutter being disposed adjacent the measuring interface when the measuring interface is in an inoperable state, and for projecting the exposed measuring interface outward of the housing.

* * * * *